(12) United States Patent
Fox

(10) Patent No.: US 10,548,762 B1
(45) Date of Patent: Feb. 4, 2020

(54) PROPHYLACTIC DEVICE

(71) Applicant: Thomas Jesse Fox, Austin, TX (US)

(72) Inventor: Thomas Jesse Fox, Austin, TX (US)

(*) Notice: Subject to any disclaimer, the term of this patent is extended or adjusted under 35 U.S.C. 154(b) by 0 days.

(21) Appl. No.: 16/359,712

(22) Filed: Mar. 20, 2019

(51) Int. Cl.
A61F 6/06 (2006.01)
A61F 6/04 (2006.01)

(52) U.S. Cl.
CPC ........ A61F 6/065 (2013.01); A61F 2006/048 (2013.01)

(58) Field of Classification Search
CPC ....... A61F 6/065; A61F 6/04; A61F 2006/048
See application file for complete search history.

(56) References Cited

U.S. PATENT DOCUMENTS

| | | | | |
|---|---|---|---|---|
| 5,269,320 A * | 12/1993 | Hunnicutt | ............... | A61F 6/065 128/830 |
| 5,596,997 A | 1/1997 | Abadi | | |
| 6,298,853 B1 * | 10/2001 | Blake | ........................ | A61F 6/04 128/844 |
| 8,236,370 B2 | 8/2012 | Moench | | |
| 2004/0000315 A1 * | 1/2004 | Al-Salem | .................. | A61F 6/04 128/844 |
| 2004/0107969 A1 * | 6/2004 | Tam | ........................ | A61F 6/065 128/830 |
| 2005/0016546 A1 * | 1/2005 | Pohlman | ................... | A61F 6/04 128/844 |
| 2016/0051399 A1 * | 2/2016 | Tang | ........................ | A61F 6/065 128/830 |

FOREIGN PATENT DOCUMENTS

FR 2750854 A1 * 1/1998 ............. A61F 6/065

OTHER PUBLICATIONS

FR 2750854 Machine Translation; Espacenet, retrieved Apr. 19, 2019; p. 1-7 (Year: 2019).*

* cited by examiner

Primary Examiner — Kari K Rodriquez
(74) Attorney, Agent, or Firm — Sprinkle IP Law Group

(57) ABSTRACT

Prophylactic devices that have a flexible sheath, and an annular retainer portion with an adhesive surface to adhere to the skin and keep the device in place. The sheath is closed at the distal end and has an opening at a proximal end. The retainer portion is connected to the sheath at the proximal end, and surrounds the opening of the sheath. The adhesive surface may be formed by an adhesive substance or other means and may seal all or part of the retainer portion against the skin. The retainer portion may conform to the skin and/or have molded features. One embodiment includes backing and cover layers which adhere to the device to form a protective pouch or package which contains the sheath and lubricants on the sheath.

15 Claims, 3 Drawing Sheets

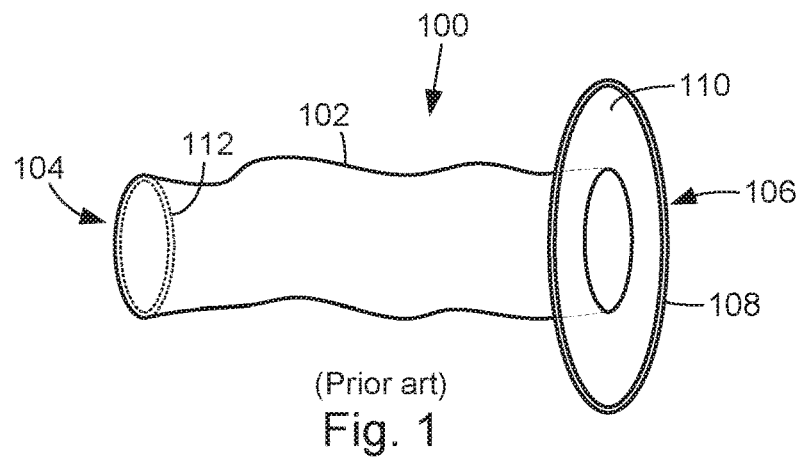
(Prior art)
Fig. 1
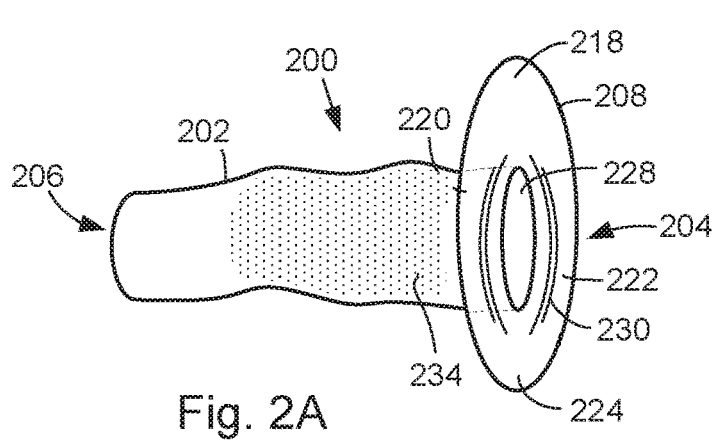
Fig. 2A
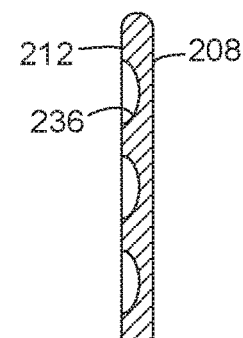
Fig. 2B
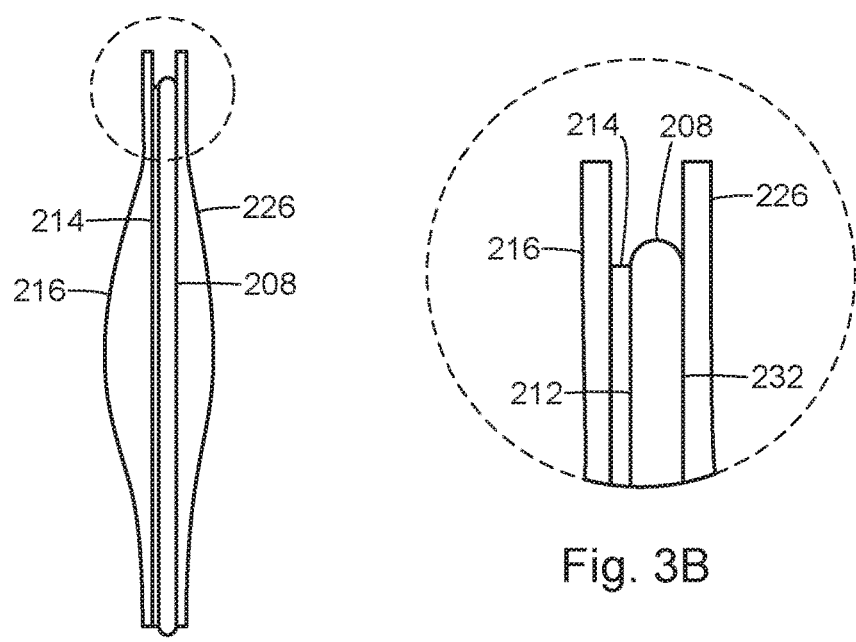
Fig. 3A
Fig. 3B

PROPHYLACTIC DEVICE

BACKGROUND

Field of the Invention

The invention relates generally to prophylactic devices for use during sexual intercourse.

Related Art

Female condoms (also known as internal condoms) are devices that are used during sexual intercourse as barrier contraceptives. Female condoms are worn internally by the female partner and provide physical barriers which prevent transmission of body fluids. These devices reduce the risk of sexually transmitted infections such as gonorrhea, syphilis, and HIV, HPV, Chlamydia, Genital Herpes, Hepatitis C as well as potential next-generation HIV-like infections that may evolve into a pandemic. Female condoms can also reduce the risk of unintended pregnancy.

The female condom is a thin, soft, loose-fitting sheath that is open at one end (referred to herein as the proximal end) and closed at the other (referred to herein as the distal end). Conventionally, the sheath has a somewhat stiff but flexible ring at each end. The ring at the closed end of the sheath is used to insert the condom inside the vagina and to hold it in place during intercourse. The rolled outer ring at the open end of the sheath remains outside the vagina and covers part of the external genitalia. Female condoms may come in various sizes.

Female condoms may be used for a number of reasons. For instance, male sexual partners may refuse to use male condoms because of a loss of sensation and the resulting reduction in their sexual performance. Because female condoms do not fit tightly against the male genitalia, their movement and perceived "rustling" noises created by the female condoms may be considered distracting. Some men may also find the appearance of the ring at the proximal end of the female condom, which remains outside the vagina, to be unattractive. It is also possible for this external ring to be pushed aside during intercourse, allowing penetration of the vagina outside the sheath of the condom.

It would be desirable to provide an improved female condom that reduces or eliminates one or more of the problems associated with conventional female condoms.

SUMMARY OF THE INVENTION

This disclosure is directed to a prophylactic device that has a flexible sheath, and an annular retainer portion with an adhesive surface to adhere to the skin and keep the device in place. The sheath is closed at the distal end (which is inserted into the vagina) and has an opening at a proximal end. The sheath may be elongated, or it may have other, more pouch-like shapes. The sheath may or may not have lubricants provided on its interior and exterior surfaces. In one embodiment, the lubricant on the exterior of the sheath has a higher viscosity than the lubricant on the interior of the sheath. The exterior surface of the sheath may have a surface texture that increases the sheath's surface area, which may increase friction between the sheath and the vaginal wall, thereby reducing movement between them. The exterior surface of the sheath may also have features (e.g., cilia or micro-hairs) that are capable of causing movement between the sheath and an interior wall of the vagina to be predominantly in a preferred direction (i.e., into the vagina, rather than out of the vagina).

The annular retainer portion is connected to the sheath at the proximal end, and surrounds the opening of the sheath. The adhesive surface on the annular retainer portion is distal-facing (toward the sheath and the body, and is capable of adhering to the skin around the opening of the vagina. The adhesive surface on the retainer portion may be formed by providing a layer of adhesive on the distal-facing surface of the retainer portion. Another alternative would be for the adhesive surface to be formed by providing a plurality of concave features on the surface so that when the retainer portion is pressed against the skin and released, the concave features maintain suction against the skin and adhere the retainer portion to the skin. The adhesive surface may be capable of sealing all or part (e.g. upper and lateral sections) of the retainer portion against the skin. The retainer portion may be a thin, flexible material, so that when it is adhered to the skin, it conforms to the shape of the skin to which it is adhered. Alternatively, the proximal-facing surface of the retainer portion may be formed to resemble external genitalia The prophylactic device may include a backing layer which is removably adhered to the adhesive surface, so that it forms at least a portion of a container for the sheath. The prophylactic device may also include a cover layer which is removably adhered to the proximal-facing surface of the retainer portion of the device, so that it forms at least a portion of the container for the sheath. The cover layer may be somewhat stiff so that when it is in place, it allows the device to be applied as a patch. When the backing layer is adhered to the adhesive surface, a first lubricant may be contained between the backing layer and the sheath. Similarly, when the cover layer is adhered to the proximal-facing surface of the retainer portion, a second lubricant may be contained between the cover layer and the sheath. A portion of the cover layer (e.g., a perimeter portion) may be removable so that the woman can wear it with greater comfort for a while before sex, while a center portion remains in place to keep the device closed and clean, with the male lubricant contained between the sheath and the center portion of the cover layer.

Numerous alternative embodiments are also possible.

BRIEF DESCRIPTION OF THE DRAWINGS

Other objects and advantages of the invention may become apparent upon reading the following detailed description and upon reference to the accompanying drawings.

FIG. 1 is a diagram illustrating a female condom in accordance with the prior art.

FIGS. 2A and 2B are diagrams illustrating a perspective view (FIG. 2A) and a partial cross-sectional view (FIG. 2B) of a prophylactic device in accordance with an exemplary embodiment.

FIGS. 3A and 3B are diagrams illustrating an exemplary embodiment of a prophylactic device in a package formed by removable backing and cover layers that are applied to the device.

Figure 4:
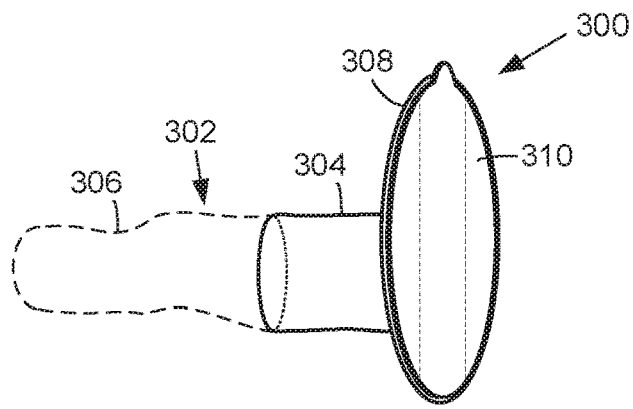
FIG. 4 is a diagram illustrating a perspective view of a prophylactic device in accordance with an alternative embodiment.

While the invention is subject to various modifications and alternative forms, specific embodiments thereof are shown by way of example in the drawings and the accompanying detailed description. It should be understood, however, that the drawings and detailed description are not intended to limit the invention to the particular embodiment which is described. This disclosure is instead intended to cover all modifications, equivalents and alternatives falling within the scope of the present invention as defined by the appended claims. Further, the drawings may not be to scale, and may exaggerate one or more components in order to facilitate an understanding of the various features described herein.

DETAILED DESCRIPTION OF EXEMPLARY EMBODIMENTS

One or more embodiments of the invention are described below. It should be noted that these and any other embodiments described below are exemplary and are intended to be illustrative of the invention rather than limiting.

As described herein, various embodiments of the invention comprise prophylactic devices for use during sexual intercourse. More specifically, these embodiments include female condoms that have a pouch or sheath with an opening that is surrounded by what is generally a thin, flat, annular portion that has an adhesive on one side which allows it to be adhered to the skin outside the opening of the vagina. When the device is used, the adhesive surface keeps it in place and prevents penetration of the vagina outside the protective barrier of the sheath. It should be noted that "annular" is used here to refer to a shape that has an outer portion with a central opening through it. The outer portion may be circular, oval, or any other shape, and is preferably designed to enhance the comfort of the user.

In one embodiment, the inventive condom is packaged with peel-off backings on both sides of the device. The backing on the adhesive surface covers the adhesive until the device is used. The backing also serves to contain and protect the sheath, and to contain a female lubricant on this (female-facing) side of the sheath. One or both of the lubricants may have anti-microbial, anti-viral and spermicidal properties. The peel-off backing on the other side of the annular portion of the device also serves to contain and protect the opposite side of the sheath, and to contain a male lubricant on this (male-facing) side of the sheath. Additional details of exemplary embodiments are provided below.

Embodiments of the present invention may provide a number of benefits. For example, because the present prophylactic device is used by women, they are empowered to choose when the device will be used. Further, the present device may be more secure and reliable than conventional female condoms. Still further, the present device may be better fitting and consequently less distracting than conventional female condoms. Because the present devices use adhesive surfaces which create a seal against the skin, they may provide an improved barrier against transmission of bodily fluids which may result in pregnancy or sexually transmitted infections, as well as menstrual fluid. This may make sexual relations less "messy" and may facilitate or encourage relations during a woman's menstrual cycle. The adhesive may also have anti-microbial, anti-viral and spermicidal properties to help prevent pregnancy or sexually transmitted infections. Various embodiments of the present prophylactic devices may include features that are intended to enhance sexual pleasure for both men and women.

Referring to FIG. 1, a conventional female condom is depicted. This figure is shown to help illustrate some of the differences between the conventional female condom and embodiments of the present invention. In this figure, it can be seen that the conventional female condom 100 has an elongated sheath 102 which has a closed end 104 (the distal end) and an open end 106 (the proximal end). Sheath 102 has a portion 110 with an enlarged diameter at the proximal end, and a semirigid ring 108 is formed at the outer perimeter of enlarged portion 110. Ring 108 is used to maintain the position of the sheath after it is inserted into the vagina or rectum, and to prevent proximal end 106 of the sheath from accidentally being moved into the vagina or rectum. A smaller semirigid ring 112 is provided at distal end 104 of the sheath. Smaller ring 112 is used to keep the distal end of the sheath positioned within the body after the female condom is inserted.

Referring to FIGS. 2-3, a prophylactic device (female condom) in accordance with one exemplary embodiment of the present invention is shown. The overall structure of device 200 is similar to that of the conventional female condom, in that it has a thin, flexible sheath 202 with an open proximal end 204 and a closed distal end 206. (While it may have any suitable shape (for example, an elongated shape similar to a male condom, or a shorter, pouch-like shape), this component will be referred to herein as a "sheath".) An enlarged retainer portion 208 is provided at proximal end 204 to keep the device in place after it has been inserted into the vagina or rectum. Although not included in this embodiment, some embodiments may have a small, semirigid ring at distal end 206 of the sheath in order to maintain the position of the distal end (and thereby keep the sheath extended) within the body.

While it is typically preferred in male condoms to minimize the thickness of the sheath (which is intended to enhance the wearer's sensitivity), the nature and use of the present device allows it to be made with heavier or thicker material. This makes the device far less likely to break, hence safer to use.

It should be noted that embodiments of the present prophylactic device can be used both vaginally and anally. Therefore, for the purposes of this disclosure, references to the use of these devices with respect to either the vagina or rectum should be construed to include both. Embodiments that are intended to be used anally may differ in shape with respect to vaginal embodiments, in that retaining portion may be more round, and the sheath may be more elongated and cylindrical. It may also be desirable for these embodiments to have a bit greater adhesion between the retaining portion and the skin.

One of the distinguishing features of this embodiment is that the enlarged retainer portion 208 does not have a semirigid ring at its perimeter, as is necessary in the prior art device. Such a ring is not necessary because retainer portion 208 has an adhesive surface which is adhered to the skin to keep the retainer portion (hence the proximal end of the prophylactic device) in position at the opening of the vagina. Because the device uses an adhesive surface rather than a large, semirigid ring to keep the proximal end of the sheath from entering the vagina, the proximal end is not loose when the device is used, and consequently does not create the distracting movement and sounds of the conventional female condom, which may make sexual relations less enjoyable and therefore make the conventional device less desirable and less likely to be used.

In one embodiment, retaining portion 208 is very thin and, when adhered to the skin, will substantially conform to the skin. This makes the device less noticeable and, in some cases the male partner may not even be aware that the female partner is wearing the device. The proximal-facing surface 232 of retaining portion 208 may be textured, or may have textural features (e.g., 230) which are intended to make the device more closely resemble the woman's external genitalia. This may be thought of as similar to the application of prosthetics in theatrical settings, wherein adhesive is used to secure the prosthetics (which may be made of latex or similar material) to the wearer's skin, allowing the prosthetics to be applied and removed on a daily basis, often to sensitive facial skin. The textural features may also provide stimulation during sexual relations.

One embodiment uses a layer of contact adhesive 214 on the distal-facing side 212 of retainer portion 208. The contact adhesive should be strong enough that the retainer portion remains in place during sexual relations, but should also be easy to remove when the relations are finished. There may be a variety of adhesives that are suitable for this purpose, such as those that are used on adhesive bandages. The surface of the adhesive layer can be textured so that there is increased surface area allowing for better adhesive effect. The material (e.g., latex) of the device under the adhesive may be textured as well. A textures surface may allow for more thicker, gel-like adhesives. A backing layer 216 consisting of paper or another suitable material is initially adhered to the contact adhesive layer 214, and is removed from the adhesive layer immediately prior to using the device.

For purposes of this disclosure, "distal-facing" refers to the side of the retainer portion that faces the distal end of the prophylactic device. "Proximal-facing" refers to the side of the retainer portion that faces away from the distal end of the prophylactic device and away from the body when the device is worn by the user.

In some alternative embodiments, it may not be necessary to use an adhesive substance to adhere the retainer portion to the skin. For example, it may be possible to incorporate concave features 236 on the distal-facing surface 212 of the annular retainer portion 208 which can be compressed and then released to create a vacuum effect that adheres the surface to the skin. effectively, these features act as miniature suction cups which adhere the retainer portion to the skin. In some embodiments, the distal-facing surface of the retainer portion may be textured so that it is less likely to slide along the surface of the skin, without actually using an adhesive or suction-creating features.

In one embodiment, adhesive layer 214 extends all the way around the perimeter of retainer portion 208, so that when the prophylactic device is used, a seal is created between the retainer portion and the user's skin around the entire perimeter of the retainer portion. In another embodiment, the adhesive is located on the upper (218) and lateral (220, 222) segments of retainer portion 208, but not on a lower (224) segment of the retainer portion. This embodiment allows fluid to flow out of the woman's vagina near the lower segment (224) of the retainer portion. In this embodiment, lower segment 224 of the retainer portion may form a flap against the skin that acts as a one-way valve so that a lower pressure is formed on the female side of the device, helping to keep it in place.

In one embodiment, backing layer 216 covers only the areas in which adhesive layer 214 is present around the perimeter of retainer portion 208. The backing layer may, for example, have an annular shape that covers a ring-shaped adhesive layer. In a preferred embodiment, however, backing layer 216 covers the entirety of the distal facing portion of the prophylactic device. In this embodiment, the center portion of backing layer 216 serves as a cover which protects not only the distal-facing adhesive surface 214, but also sheath 202 until the backing layer is removed and the device is used. Similarly, a front, cover layer 226 may be adhered to the proximal-facing surface of the device to serve as a cover which protects this surface and opening 228 at the proximal end of sheath 202. Cover layer 226 may also give additional structure to retainer portion 208 to facilitate ease of application of the prophylactic device.

Together, backing layer 216 and cover layer 226 effectively form a pouch that contains and protects the sheath, as well as the proximal-facing and distal-facing surfaces of the retainer portion. In one embodiment, the cover layer may be segmented so that part of it can be peeled away after application. A remaining portion of the cover layer will stay in place to maintain the pouch structure that contains the sheath. This will allow the device to be worn more comfortably prior to actual use (penetration) while maintaining cleanliness.

Additionally, the pouch formed by backing layer 216 and cover layer 226 may serve to contain lubricants that are provided on the interior and exterior surfaces of the sheath (where "interior" refers to the side of the sheath that contacts the penis and "exterior" refers to the side of the sheath that contacts the vagina). The prophylactic device may have lubricant only on one side of the sheath, or it may have lubricants on both the interior and exterior surfaces. In one embodiment, different lubricants may be provided on the different surfaces of the sheath. For example, the interior of the sheath may have a first lubricant that is better suited for a penis, such as a lower-viscosity lubricant that maximizes lubricity for penetration, while the exterior of the sheath may have a second lubricant which is better suited to a vagina, such as a higher-viscosity lubricant that reduces movement of the sheath with respect to the vaginal wall. The exterior surface of the sheath may also have micro-hairs (cilia), texturing, or other features which help prevent the sheath from moving within the vagina during intercourse. Examples of these features are discussed in more detail below.

The various embodiments of the invention may have a number of variations from the specific exemplary embodiments described above. For example, for those who have multiple partners and are uncomfortable removing (peeling off) a used device and applying a new device, there is an embodiment in which the retainer portion stays in place and the sheath is replaceable with one that has a smaller adhesive portion. Some embodiments may have a stronger adhesive and/or thicker sheath material for greater protection. Some embodiments may be molded so that the proximal-facing surface is "anatomically correct" (i.e., has features that resemble the area of the vaginal opening. Some embodiments may be made of materials that have various flavors, scents and or colors. Some embodiments may have a thin barrier on the distal-facing side that holds the lubricant and sheath in place, but is designed to be ruptured, releasing the sheath and lubricant when penetration is made from the proximal-facing side.

Some embodiments may have textural features ("nubs") on the interior surface of the sheath which provide additional stimulation for the penis. Other alternative embodiments may include a porous, absorbent layer 234 on the exterior surface of the sheath that absorbs liquid as it is used. This may help to hold the device in place, and may make the fit between the device and the vagina tighter as the device absorbs the liquid. Another alternative embodiment may include small textured nubs in a region that is near the clitoris when the device is used. The device may further include a pad with small nubs that stretches and rubs the "G" spot just behind the pubis bone. The pad could be sponge-like, enlarging after insertion as it absorbs moisture. The action of penetration will simultaneously rub the pad against the g spot and stretch the device, thereby moving the nubs over the clitoris to provide additional stimulation.

While some embodiments are packaged in a manner in which the device is substantially flat (e.g., as shown in FIG. 3A), others may incorporate a structure that allows the device to be inserted like a tampon. The male (proximal-facing) side of the device side can then be made flatter, less puffy and/or more naturally shaped. An example such an alternative embodiment is depicted in FIG. 4.

Device 300 has a structure similar to that of device 200, but a part (304) of sheath 302 and the retainer portion 308 are less flexible, so that they form a structure that is capable of being easily inserted into the vagina. Thus, where sheath 202 of device 200 can be collapsed into a flat package, the structure of device the proximal part (304) of the sheath and the retainer portion 308 retain a shape similar to that of the cap and stem of a mushroom. In its packaged form, the distal part (306) of the sheath is collapsed into the proximal part (304) of sheath 302. Other features such as lubricants, textural nubs, absorbent layers, pads, etc. may also be contained in the cylindrical proximal part (304) of the sheath when the device is packaged. After the device is inserted into the vagina with retainer portion 308 adhered around the vaginal opening, cover layer 310 can be removed and penetration of the device will extend the distal part (306) of the sheath (as shown by the dashed line in FIG. 4) into the body cavity, releasing the lubricant and deploying the textural features and other features.

As noted above, the exterior surface of the sheath may have features that help prevent the sheath from moving within the vagina during intercourse. These features may also be configured to move more easily in one direction than another, so that the sheath has a greater tendency to move into the vagina, than out of it. Below are several examples of surface features that may be used on the sheath. Embodiments of the invention may use any of these features, or even a mix of different types of surface features.

Figure 5:
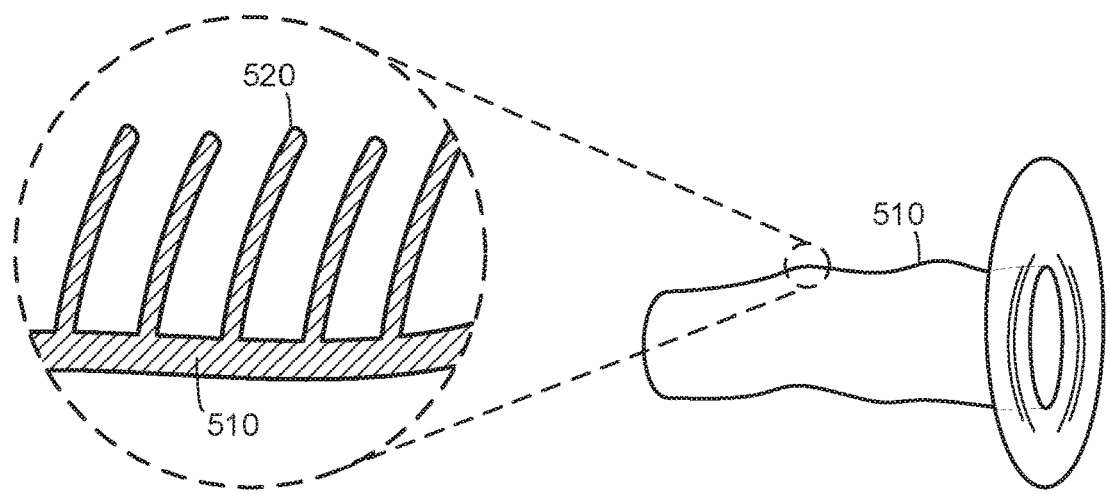
FIG. 5 is a diagram illustrating an exemplary surface texture having cilia in accordance with one embodiment.

Referring to FIG. 5, a diagram illustrating an exemplary surface texture having cilia is shown. A female condom is depicted on the right side of the figure. The sheath 510 of the female condom has cilia or micro-hairs 520 on its external surface. It can be seen from the enlarged view of the sheath on the left side of the figure that the cilia are angled and slightly curved to the right (i.e., toward the opening of the sheath). As a result, movement of the sheath and cilia against the vaginal wall will cause the sheath to have a greater tendency to move to the left (into the vagina) than to the right (out of the vagina).

Figure 6:
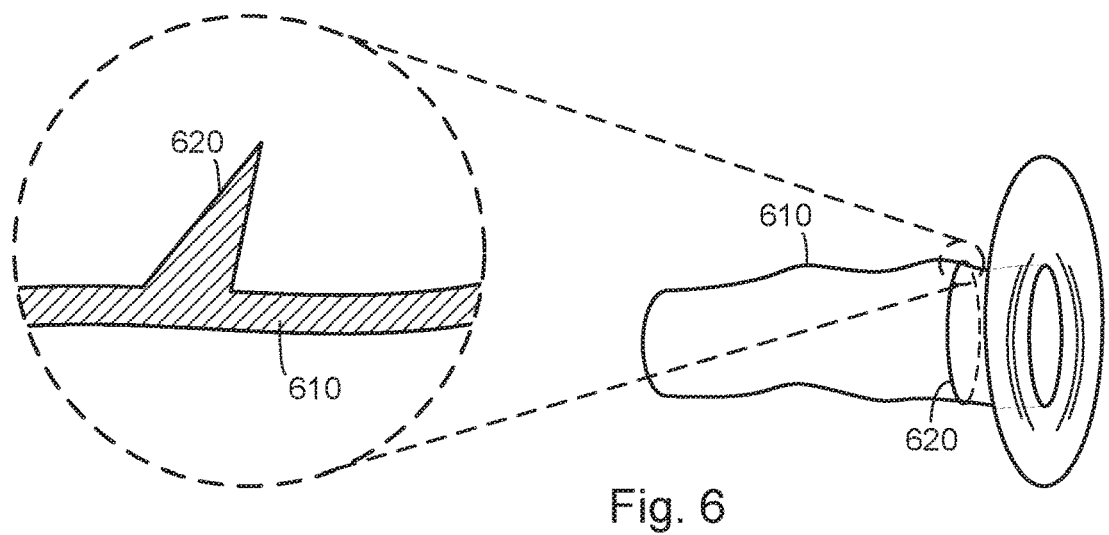
FIG. 6 is a diagram illustrating an exemplary ring-type surface structure in accordance with one embodiment.

Referring to FIG. 6, an alternative structure on the exterior of the sheath is illustrated. In this figure, the sheath 610 of the female condom has a ring 620 around its exterior. Although a single ring is depicted in the figure, alternative embodiments may have multiple rings on the exterior of the sheath. As shown in the enlarged view of the sheath on the left side of the figure, the ring has a generally triangular cross-section. The triangular structure may help to prevent the sheath from moving with respect to the vaginal wall during intercourse. Similar to the cilia of FIG. 5, the triangular structure leans slightly to the right (toward the opening of the sheath), so that the sheath will have a greater tendency to move to the left (into the vagina) than to the right (out of the vagina) as a result of movement of the sheath and ring against the vaginal wall.

Figure 7A:
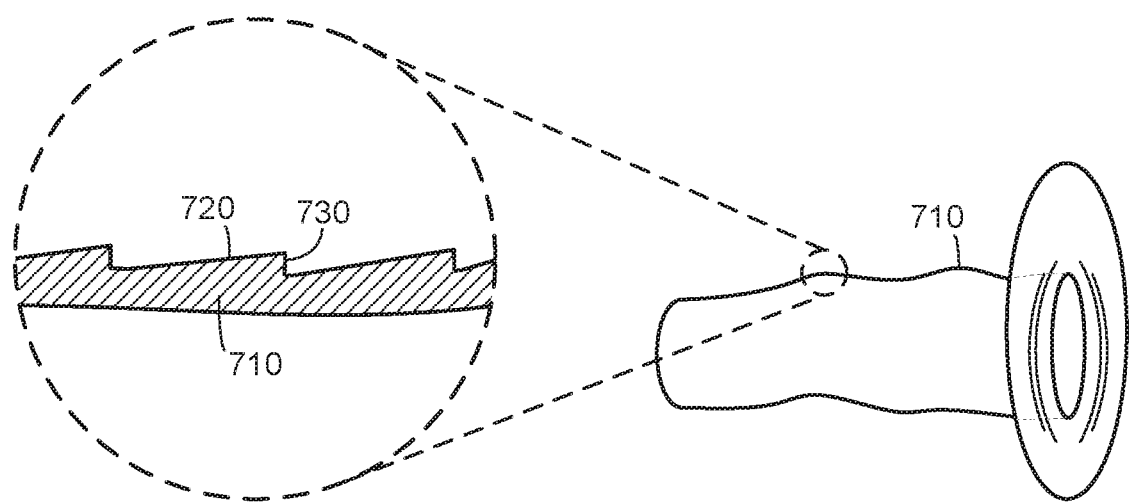
FIGS. 7A-7B are diagrams illustrating an exemplary surface texture having scale-type structures in accordance with one embodiment.
Figure 7B:
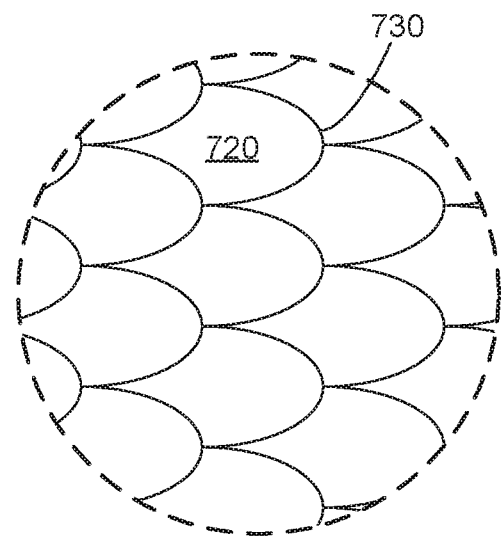

Another alternative surface structure on the exterior of the sheath is illustrated in FIGS. 7A and 7B. In this figure, the sheath has a "snakeskin" or "fish scale" texture on its exterior surface. The enlarged cross-sectional view of the sheath on the left side of the figure shows that the face 720 of each scale-shaped feature is slightly sloped, with the edges 730 having a much greater slope, so that the surface slides more easily in the direction from the edge toward the center of the feature or scale. A surface view of the texture is depicted in FIG. 7B. The snakeskin texture is preferably oriented in the direction shown in the figures, with the edge of each feature (scale) facing the opening of the sheath (to the right in the figures) and the downward-sloping face oriented toward the closed end of the sheath (to the left in the figures). It should be noted that alternative embodiments may use different shaped features, and the features need not be distinct, individual, scale-like features The benefits and advantages which may be provided by the present invention have been described above with regard to specific embodiments. These benefits and advantages, and any elements or limitations that may cause them to occur or to become more pronounced are not to be construed as critical, required, or essential features of any or all of the claims. As used herein, the terms "comprises," "comprising," or any other variations thereof, are intended to be interpreted as non-exclusively including the elements or limitations which follow those terms. Accordingly, a system, method, or other embodiment that comprises a set of elements is not limited to only those elements, and may include other elements not expressly listed or inherent to the claimed embodiment.

It should be noted that the sizes and shapes of the features on the exterior of the sheath as described above are exemplary, other sizes and/or shapes may be used in other embodiments. It should also be noted that the features are intended to be formed using a soft and flexible material (e.g., the same material used to form the sheath) so that the features will not negatively affect the comfort of the user when the device is in place.

While the present invention has been described with reference to particular embodiments, it should be understood that the embodiments are illustrative and that the scope of the invention is not limited to these embodiments. Many variations, modifications, additions and improvements to the embodiments described above are possible. It is contemplated that these variations, modifications, additions and improvements fall within the scope of the invention as detailed within the following claims.

What is claimed is:

1. A prophylactic device comprising:
   a flexible sheath which is closed at a distal end and has an opening at a proximal end;
   an annular retainer portion which is connected to the sheath at the proximal end, and which surrounds the opening of the sheath; and
   an adhesive surface on the annular retainer portion, wherein the adhesive surface is distal-facing, and wherein the adhesive surface is capable of adhering to the skin of a person's body, wherein the sheath has an interior surface and an exterior surface, wherein the exterior surface has a surface texture that causes the sheath to have a greater tendency to move with respect to an interior wall of a body cavity in a direction away from the retainer portion than toward the retainer portion and, wherein the surface texture comprises a plurality of cilia that are formed on the exterior surface of the sheath, wherein the cilia are angled toward the retainer portion.

2. The prophylactic device of claim 1, wherein the adhesive surface is capable of sealing at least an upper section and two lateral sections of the annular retainer portion against the skin and thereby preventing fluids from flowing between the skin and the upper and lateral sections of the annular retainer portion.

3. The prophylactic device of claim 1, further comprising a backing layer which is removably adhered to the adhesive surface, wherein when the backing layer is adhered to the adhesive surface, the backing layer forms at least a portion of a container for the sheath.

4. The prophylactic device of claim 3, wherein when the backing layer is adhered to the adhesive surface, the backing layer and the sheath form a first enclosed volume, wherein a first lubricant is contained in the first enclosed volume.

5. The prophylactic device of claim 3, further comprising a cover layer which is removably adhered to a proximal-facing surface of the annular retainer portion, wherein when the cover layer is adhered to the proximal-facing surface of the annular retainer portion, the cover layer forms at least a portion of the container for the sheath.

6. The prophylactic device of claim 5, wherein when the cover layer is adhered to the proximal-facing surface of the annular retainer portion, the cover layer and the sheath form a second enclosed volume, wherein a second lubricant is contained in the second enclosed volume.

7. The prophylactic device of claim 1, wherein the sheath is elongated, having an extended length from the proximal end to the distal end which is greater than a diameter of the sheath.

8. The prophylactic device of claim 1, wherein the adhesive surface on the annular retainer portion is formed by providing a layer of adhesive on the distal-facing surface of the annular retainer portion.

9. The prophylactic device of claim 1, wherein the adhesive surface on the annular retainer portion is formed by providing a plurality of concave features on the distal-facing surface of the annular retainer portion, wherein when the annular retainer portion is pressed against the skin and released, the concave features maintain suction against the skin and thereby adhere the annular retainer portion to the skin.

10. The prophylactic device of claim 1, wherein the annular retainer portion allows fluid to flow between the skin and a lower section of the annular retainer portion.

11. The prophylactic device of claim 1, wherein the annular retainer portion comprises a thin, flexible material, wherein when the adhesive surface of the annular retainer portion is adhered to the skin, the annular retainer portion conforms to the shape of the skin to which the adhesive surface is adhered.

12. The prophylactic device of claim 1, wherein a proximal-facing surface of the annular retainer portion is formed to resemble external genitalia.

13. The prophylactic device of claim 1, wherein the sheath has an interior surface and an exterior surface, wherein the interior surface has a first lubricant thereon and the exterior surface of the sheath has a second lubricant thereon, wherein the second lubricant has a higher viscosity than the first lubricant.

14. The prophylactic device of claim 1, wherein the adhesive has at least one of: anti-microbial properties; anti-viral properties; and spermicidal properties.

15. The prophylactic device of claim 1, wherein the surface texture comprises a porous, absorbent layer on the exterior surface of the sheath that absorbs liquid as prophylactic device is used, thereby making a fit between the prophylactic device and the body cavity tighter as the absorbent layer absorbs the liquid.

* * * * *